United States Patent [19]

Gamble et al.

[11] Patent Number: 4,670,384
[45] Date of Patent: Jun. 2, 1987

[54] DIAGNOSTIC REAGENT FOR SWINE TRICHINOSIS

[75] Inventors: Howard R. Gamble, Bowie; Kenneth D. Murrell, Rockville, both of Md.

[73] Assignee: The United States of America as represented by the Secretary of Agriculture, Washington, D.C.

[21] Appl. No.: 683,284

[22] Filed: Dec. 18, 1984

[51] Int. Cl.$^4$ ................ G01N 33/545; G01N 33/569; G01N 33/577

[52] U.S. Cl. .................................... 435/7; 435/172.2; 435/240; 435/948; 436/529; 436/531; 436/548; 436/811; 530/387; 530/808; 530/813; 530/815; 935/104; 935/108; 935/110

[58] Field of Search ............... 935/103, 108, 110, 104; 435/7, 172.2, 240, 948; 436/529, 531, 548, 824; 530/387, 413, 808, 813, 815

[56] References Cited

U.S. PATENT DOCUMENTS 4,468,346  8/1984  Paul et al. ............................... 435/7

OTHER PUBLICATIONS

H. R. Gamble et al., American Journal of Veterinary Research 45, 67–74, 1984.
H. R. Gamble et al., Veterinary Immunology and Immunopathology 6, 379–389, 1984.
D. S. Silberstein et al. Journal of Immunology 132, 898–904, 1984.
G. Galfre et al., Methods in Enzymology 73, 3–46, 1981.
V. Mazzola, "New Trichinosis Test—First Step to Eradication," *Agricultural Research*, p. 10 (Jun. 1984).
V. Mazzola, "Monoclonal Antibodies: Probing the Mysteries of Immunity," and Monoclonal Antibodies at Work, *Agricultural Research*, pp. 8–11, (Jan. 1984).
H. R. Gamble, "Application of Hybridoma Technology to the Diagnosis of Parasitic Disease," handed out at Second International Immunoparasitology Symposium, Aug. 3–5, 1983.
H. R. Gamble, "Application of Hybridoma Technology to the Diagnosis of Parasitic Disease, *Veterinary Parasitology* 14: 251–261 (1984).
E. J. Ruitenberg, P. A. Steerenberg, B. J. M. Brosi, and J. Buys, "Reliability of the Enzyme-Linked Immunosorbent Assay (ELISA) for the Serodiagnosis of *Trichinella spiralis* Infections in Conventionally Raised Pigs," *Journal of Immunological Methods* 10: 67–83 (1976).
H. R. Gamble, W. R. Anderson, C. E. Graham, and K. D. Murrell, "Diagnosis of Swine Trichinosis by Enzyme-Linked Immunosorbent Assay (ELISA) Using an Excretory-Secretory Antigen," *Veterinary Parasitology* 13: 349–361 (1983).
G. L. Seawright, D. Despommier, W. Zimmerman, and R. S. Isenstein, "Enzyme Immunoassay for Swine Trichinellosis Using Antigens Purified by Immunoaffinity Chromatography," *Am. J. Trop. Med. Hyg.* 32(6): 1275–1284 (1983).
F. VanKnapen, J. H. Franchimont, N. Skovgaard, J. Guidal, and S. A. Henriksen, "Husbandry, Parasitic and Other Diseases as Factors in the Reliability of the Enzyme-Linked Immunosorbent Assay (ELISA) for Detection of Trichinellosis in Pigs," Veterinary Parasitology 16: 17–22 (1984).
M. K. Showe, E. Isobe, and L. Onorato, "Bacteriophage T4 Prehead Proteinase," *J. Mol. Biol.* 107: 55–69 (1976).

*Primary Examiner*—Sidney Marantz
*Assistant Examiner*—David A. Saunders
*Attorney, Agent, or Firm*—M. Howard Silverstein; William E. Scott; Margaret A. Connor

[57] ABSTRACT

A hybrid cell formed by the fusion of a mouse spleen cell with a mouse myeloma cell secretes an IgM class antibody. The antibody is useful as a preparative reagent in the isolation of three proteins, molecular weights 45,000, 49,000 and 53,000, from the parasite *Trichinella spiralis* and is also useful as a direct diagnostic reagent is a competitive serodiagnostic test.

4 Claims, No Drawings

DIAGNOSTIC REAGENT FOR SWINE TRICHINOSIS

BACKGROUND OF THE INVENTION

1. Field of The Invention

This invention pertains to a new hybrid cell line formed by the fusion of a mouse myeloma cell with a mouse spleen cell and to an antibody molecule secreted by the hybrid cell.

2. Description of Material Information

The enzyme-linked immunosorbent assay (ELISA) has been widely used for the diagnosis of trichinosis in swine. A crude extract of the parasite has been used as the antigen in this test in most cases. The major problem arising from the use of this complex antigenic mixture has been false positive reactions due to interactions with antibodies directed against other common swine nematodes, J. Immunol. Meth. 10, 67–83, 1976; Vet. Parasitol. 9, 117–123, 1981.

Previous attempts to refine the antigen preparation for use in the ELISA have followed conventional biochemical separation techniques. These studies have yielded complex antigen mixtures with improved utility in the ELISA. However, no information is available on rates of false-positive reactions with sera from swine with other nematode infections. Additionally, the antigen isolation steps are complex and costly.

The present invention eliminates false-positive reactions in sera of swine harboring other common nematode parasites. It makes the isolation of the antigen for use in the indirect ELISA a one-step procedure Alternatively the monoclonal antibody may be used directly in a competitive ELISA.

SUMMARY OF THE INVENTION

An object of the invention is to provide a new hybrid cell by fusion of a mouse myeloma cell and a mouse spleen cell.

Another object of this invention is to provide a hybridoma that secretes an antibody molecule that is useful in isolating proteins used in a serodiagnostic test for *Trichinella spiralis*.

A further object is to provide a hybridoma that may be used directly in a competitive serological test for *Trichinella spiralis*.

According to this invention, the above objects are accomplished by a hybridoma designated as $7C_2C_5$ produced by the fusion of a mouse myeloma cell with a mouse spleen cell and by an antibody molecule secreted by the hybridoma.

DESCRIPTION OF THE INVENTION

The invention is a hybrid cell line or hybridoma formed by the fusion of a mouse myeloma cell, 3×63 Ag 8.653, with a mouse spleen cell. The mouse spleen cell donor was infected with 200 infective *Trichinella spiralis* larvae 35 and seven days prior to use in the cell fusion. The cells were fused by standard methods using polyethelyne glycol. The hybrid cell was twice cloned and preserved by freezing in liquid nitrogen. The hybridoma secretes a single type of antibody molecule which is an IgM immunoglobulin molecule and which identifies and may be used to isolate a useful diagnostic antigen for swine trichinosis. Therefore, the invention is useful to determine if swine are infected with *Trichinella spiralis*. The hybridoma produced antibody molecule may be used as a process reagent to isolate by affinity chromatography proteins used in a serodiagnostic test or it may be used directly in a competitive serologic test.

The antibody molecule may be used as an affinity ligand to isolate three proteins from an extract of the parasite *Trichinella spiralis*. Hybridoma $7C_2C_5$-produced antibodies are covalently linked to a cross-linked dextran gel and used as an affinity ligand to isolate the three specific proteins from a crude mixture. The crude mixture may be proteins from homogenized *Trichinella spiralis* parasites or secretory products obtained by culturing the parasite in tissue culture media. The crude protein extract is then passed over the affinity column in a buffer system of 100 mM Tris (pH 8.0). Specifically bound proteins are then eluted with 0.2M glycine (pH 2.0). The three proteins so isolated, designated Ts.53, Ts.49, Ts.45, molecular weights 53,000, 49,000 and 45,000, contain the only antigen epitopes known to be unique to the parasite *Trichinella spiralis*. The unique properties were identified using antibody from hybridoma $7C_2C_5$. Because of the uniqueness of this antigen epitope to the parasite it is the only diagnostic antigen known to eliminate false-positive reactions (cross-reactions) in a serodiagnostic test for swine trichinosis. In this capacity the isolated antigen is used in an indirect ELISA for the specific diagnosis of swine trichinosis.

As a direct diagnostic reagent, hybridoma $7C_2C_5$-produced monoclonal antibody is labeled with biotin and used in a competitive ELISA test. A crude protein extract is coated on a plastic surface. Biotin-labeled monoclonal antibodies are then mixed with a swine serum sample, and laid over the coated plastic surface. Biotin-labeled monoclonal antibodies bind to the protein mixture on the plastic surface; however, when swine serum antibodies resulting from a *Trichinella spiralis* infection are present, they compete for binding sites in the protein mixture, resulting in less biotin-labeled monoclonal antibody being bound. This inhibition of maximum binding indicates the presence of *T. spiralis* specific antibodies. An avidin-enzyme reagent is then applied over the plastic surface. Avidin has a high affinity for biotin and hence is used as part of a detection system for bound biotin-labeled monoclonal antibody. Finally, bound avidin-enzyme is detected by the addition of an enzyme substrate which changes color to indicate the presence of enzyme. The indication of a *Trichinella spiralis*-infected pig is a decrease in the color intensity compared to controls. The advantage of the antibodies produced by hybridoma $7C_2C_5$ is that a unique *T. spiralis* antigen epitope is recognized exclusively. Cross-reactions or false-positive reactions are eliminated with this antigen reagent.

In addition, since antigens Ts.53, Ts.49, and Ts.45 have been shown to have potential as a vaccine for *Trichinella spiralis* infection, isolation of these proteins as described above may be applicable to the preparation of a vaccine.

Hybridoma cell line $7C_2C_5$ has been deposited in the American Type Culture Collection, Rockville, Md., and has been assigned the designation HB 8678.

The hybridoma of this invention and the antibody molecule secreted by the hybridoma were produced and examined by the following procedures.

*Trichinella spiralis* was maintained in male Sprague-Dawley rats by serial passage. Muscle larvae ($L_1$) were recovered by pepsin-HCl (1% each) digestion of eviscerated, ground rat carcasses and washed by settling through several changes of water. Adult worms were recovered from rat intestines seven days postinoculation using a modified Baermann apparatus with Hank's Balanced Salt solution at 37° C.

Production of hybridomas—Three- to 4-month-old female Balb/cJ mice were each given an oral inoculum of 200 infective *Trichinella spiralis* $L_1$. They each were reinoculated four weeks later with 200 larvae. Mice were killed after seven days and the spleens removed.

Cell fusions were performed by the methods of Kennett with some modifications, Monoclonal antibodies, Plenum Press, N.Y., 1980, pg 365–367. Briefly, mouse spleens were removed aseptically into Dulbecco's Modified Eagles medium (DMEM) with 2 mM glutamine, 1 mM sodium pyruvate, 10 mM HEPES buffer, 50 U/ml penicillin and 50 μg/ml streptomycin (complete DMEM) plus 10% fetal calf serum (FCS), and a single cell suspension was prepared using glass slides. Red blood cells were lysed by incubation of the spleen cells in 0.17 M ammonium chloride buffer for ten minutes at 4° C. after which the cells were washed in DMEM and counted.

Myeloma cells P3-X 63-Ag8, an inherent $IgG_1k$ secretor or P3-X 63-Ag8 653, a non-secreting variant) were harvested from log phase cultures and $10^7$ cells mixed with $10^8$ spleen cells in a round bottom glass tube. After washing in DMEM, 1 ml of 50% polyethylene glycol (PEG) 1000 in DMEM (42° C.) was added and the pellet resuspended by tapping the tube. The cell mixture was immediately centrifuged at 500 g for three minutes, held two minutes, and then 5 ml of DMEM added slowly. The cells were held another two minutes, gently resuspended, centrifuged and resuspended in HAT selective medium (complete DMEM, 10% NCTC-109, 20% FCS, $10^{-4}$ M hypoxanthine, $4\times10^{-7}$ M amethopterin and $1.6\times10^{-5}$ M thymidine$_d$) at $3.3\times10^5$ myeloma cells/ml. Cells were plated into three $15\times100$ mm petri dishes, incubated overnight at 37° C. in a 10% $CO_2$ atmosphere and then dispensed into 96 well plates at a concentration of $1.67\times10^4$ in 0.1 ml/well. Fused cells were fed twice a week with HAT medium and wells showing growth, usually after two weeks, were screened for antibody secretion in an ELISA assay as noted below using an extract of homogenized *T. spiralis* $L_1$ as antigen. Hybrids positive for *T. spiralis* antigen were cloned by limiting dilution in complete DMEM with 20% FCS using mouse thymocytes as feeder cells. Monoclonal antibody was recovered either from culture supernatants or from ascites produced in pristane primed Balb/cJ mice by intraperitoneal injection of $5\times10^6$ hybrid cells.

Determination of antibody specificity—Hybridoma antibodies produced against *T. spiralis* were screened against a variety of parasite antigen preparations in an ELISA test. Crude saline extracts were prepared from *T. spiralis* $L_1$ (CWE) and adult worms by homogenation in a Potter-Elvejin tissue grinder at 4° C. followed by centrifugation at 20,000 g. A *T. spiralis* excretory-secretory (ES) antigen was prepared by cultivation of $L_1$ in Liebowitz medium L-15 as described in Vet. Parasitology 13, 349–361, 1983. Saline extracts of *Ascaris suum* adults, larvae ($L_3$,4) and eggs were obtained from the Animal Parasitology Institute (API), Beltsville, Md. Saline extracts of *Strongyloides ransomi* larvae ($L_3$) and *Stephanurus dentatus* adults were also obtained from API. A crude saline extract of *Trichuris suis* was prepared by homogenization, as described above, of adult worms recovered from the large intestine of naturally-infected pigs at slaughter. All extracts were clarified by centrifugation at 20,000 g and their protein content determined by the methods described in J. Biol. Chem. 193, 265–275, 1951. For the ELISA, 96-well round-bottom polystyrene plates ("Microtiter" plates by Dynatech Laboratories, Inc.) plates were coated with antigen (5 μg in 0.1 ml per well) in 0.1 M carbonate buffer (pH 9.6) overnight at 4° C. Wells were post-coated with 3% BSA in saline. Following this step and all subsequent steps, wells were washed three times with Dulbecco's phosphate buffered saline (PBS) containing 0.05% polyoxyethylenesorbitan monolaurate ("Tween" 20 by Union Carbide). Each of the following reagents was added sequentially (100 μl per well) and incubated for one hour at room temperature: hybridoma cell supernatant; rabbit anti-mouse light-chain (k) (diluted 1:500 in PBS-Tween); and goat anti-rabbit IgG conjugated to horseradish peroxidase (diluted 1:1000 in PBS-Tween). Bound enzyme was visualized by the addition to each well of 100 μl of 5' aminosalycylic acid (0.8 mg/ml) with 0.005% $H_2O_2$ (pH 5.6). After 30 minutes plates were read in a Titertek Multiscan. Values greater than $5\times$ the $P3\times$ control were considered positive.

Characterization of monoclonal antibodies—Class and subclass of secreted monoclonal antibodies were determined by Ouchterlony gel diffusion of concentrated culture supernatants against goat anti-mouse heavy-chain specific reagents. The presence of the μ chain of monoclonal IgM was confirmed by SDS polyacrylamide gel electrophoresis and autoradiography of reduced $S^{35}$-labelled monoclonal antibodies obtained by growth of $2\times10^6$ cells per ml in methionine-free RPMI-1640 with 25 μCi/ml of $S^{35}$ methionine, Immunology 21, 1065–1071, 1971.

The agglutinin property of monoclonal IgM was assessed using antigen coated sheep red blood cells (SRBC's). Freshly collected SRBC's were treated with 0.01% tannic acid and coated with *T. spiralis* $L_1$ ES antigen (0.5 mg per ml of 5% SRBC's in PBS, pH 6.4), then washed and stored as a 5% suspension in PBS (pH 7.2) at 4° C. Agglutination was performed in round-bottom 96-well microtiter plates. Fifty μl of the 5% SRBC suspension was added to wells followed by the addition of 50 μl of ascites at 10-fold dilutions. Plates were incubated overnight and the endpoint of agglutination determined visually. To determine the influence of reduction on agglutination, antibody in ascites fluid was treated by mild cysteine reduction followed by alkylation, according to the methods described in J. Immunol. 115, 223–229, 1975. This technique has been shown to reduce pentameric IgM to monomers without significant reduction of interchain disulfide bonds. Untreated ascites fluid was included as a control for hemagglutination of coated SRBC's.

The molecular weight of secreted IgM was assesed by gel filtration chromatography of 50% $NH_4SO_4$ precipitates from mouse ascites on cross-linked agarose gel filtration medium ("Sepharose" CL-4B by Pharmacia) equilibrated in PBS (pH 7.2). Molecular weight markers included mouse serum immunoglobulins treated in the same manner. Column fractions were assayed directly for anti-*T. spiralis* activity in an ELISA performed as above.

To demonstrate the antigen specificity of monoclonal antibodies, immunoreplicate electrophoresis was performed essentially by the methods described in J. Mol. Biol. 107, 55–69, 1976. *Trichinella spiralis* ES products were separated in 5–20% gradient SDS-polyacrylamide gels under reducing conditions. Following electrophoresis, gels were overlayed with 1% agarose containing ascites fluid (1:5) and precipitin bands allowed to develop for two days at 4° C. Agarose overlays were then floated free from the acrylamide and washed for three days in 1.5% saline at 4° C. Overlays were dried between filter paper and gel bond film at 60° C., stained with Commassie Blue R-250, and compared to molecular weight markers.

Immunological detection of antigens blotted onto nitrocellulose (western blots) was performed essentially by the methods described in Prod. Nat'l. Acad. Sci. 76, 4350–4354, 1979. Excretory-secretory products were separated in 5-20% SDS-polyacrylamide gels and electroblotted onto nitrocellulose in a Transblot cell according to the manufacturer's instructions. Strips of nitrocellulose corresponding to gel lanes were cut and unreacted sites blocked by incubation in 10 mM Tris buffer (pH 7.4) with 0.9% NaCl, 3% bovine serum albumin (BSA) and 0.4% Tween-20. Following blocking, and all subsequent steps, strips were washed three times in PBS (pH 7.2) with 0.2% BSA and 0.4% Tween-20 (wash buffer). Sequential incubations were then performed in: ascites fluid (1:10 dilution in wash buffer) for one hour at room temperature and one hour at 4° C.; rabbit anti-mouse light chain (k) (1:100 dilution in wash buffer) for one hour at room temperature and 72 hours at 4° C.; and goat anti-rabbit IgG conjugated to horseradish peroxidase (1:1000 dilution in wash buffer) for two hours at room temperature. Bound enzyme was visualized by incubation of strips in 0.005% $H_2O_2$ with 5'-ASA as indicator (0.8 mg/ml, pH 5.6).

Reactivity of monoclonal antibodies with parasite sections—Diaphragm tissue from rats inoculated with *T. spiralis* as described above were collected 28 days postinoculation. Tissues were formalin-fixed, embedded in parafin, sectioned at 5 µm and treated as follows. For morphological observation and stichocyte identification, sections were stained with toluidine blue as described in J. Parasitol. 62, 775–785, 1976. For antigen localization sections were stained by the immunoperoxidase procedure of Hsu et al, J. Histochem. Cytochem. 29, 577–580, 1981, using the biotin-avidin-peroxidase staining system ("Vectastain" ABC kit by Vector Laboratories, Inc.) with the following modifications. Primary antibody, consisting of a 50% ammonium sulfate fraction of ascites fluid from hybridoma $7C_2C_5$ or P3X, was biotinylated according to the methods described in J. Histochem. Cytochem. 28, 771–776, 1980. Worm sections were incubated for one hour in biotinylated primary antibody prior to addition of the avidin-peroxidase conjugate.

Reactivity of monoclonal antibodies with live parasites—Freshly isolated *T. spiralis* $L_1$ were washed several times in saline and incubated (30 worms/200 µl) in 96 in 96 well microtiter plates containing either ascites fluid from a *T. spiralis*-specific monoclonal antibody, ascites fluid from P3X, and normal or immune swine sera as described below. Plates were incubated at 37° C., examined periodically for precipitation reactions and photographed.

Affinity isolation of antigens—Ascites fluid was partially purified by precipitation with 50% ammonium sulfate. Precipitated antibody diluted to 2 mg/ml in 0.1 M $NaHCO_3$ with 0.5 M NaCl (ph 8.3) was coupled to CNBr-activated Sepharose 4B according to the manufacturer's instructions. Following blocking of unreacted sites, the column was pre-eluted with 0.2M glycine (pH 2), then equilibrated in 0.1 M Tris (pH 8). Antigen consisting of an ES preparation (4 mg in 4 ml) in 0.1 M Tris (pH 8) was passed over the column and eluted until absorbance at 280 nm had returned to baseline. Bound antigen was eluted with 0.2 M glycine (pH 2), dialyzed into PBS, concentrated on a YM-5 membrane under pressure, and stored at −20° C.

ELISA for *T. spiralis* antibodies in swine sera Crude worm extract (CWE) (10 µg/ml) or affinity isolated antigen (5 µg/ml) in 0.1 M carbonate buffer (pH 9.6) was used to coat 96-well microtiter plates. An ELISA for *T. spiralis*-specific antibodies was performed essentially as described in Veterinary Parasitology 13, 349–361, 1983. Briefly, 100 µl of swine sera diluted 1:100 in PBS-Tween 20 was added to wells for 30 minutes. Following washing, 100 µl of a rabbit anti-pig IgG heavy-chain specific reagent, Vet. Parasitol. Supra, was added (30 minutes), washing was repeated and a peroxidase-labelled goat anti-rabbit IgG (100 µl) was added for another 30 minutes. Bound enzyme was visualized by the addition of 0.005% $H_2O_2$ with 5'-ASA as indicator (0.8mg/ml, pH 5.6). Values greater than 5×the normal pool of swine sera were considered positive.

Swine sera tested by ELISA consisted of the following: a normal pool collected from eight pigs (two-months-old) from the specific pathogen-free (SPF) herd maintained at API; 30 sera from pigs of the API herd which had received 400 *T. spiralis* $L_1$ per pound body weight at two months of age and had been bled six months postinoculation; and 35 sera from farm-raised pigs collected from slaughterhouses; digestion-negative for *T. spiralis* but known to give false-positive reactions in an ELISA test with a crude extract of *T. spiralis*, Vet. Parasitol. supra.

Production and specificity of monoclonal antibodies—Two separate fusions resulted in 49 of 1104 wells producing antibodies specific for *T. spiralis* $L_1$ antigen. Seventeen of the most rapidly growing hybrids from this group were selected, cloned by limiting dilution, and expanded. Isotypes of secreted antibodies in this group included $IgG_1$ (3), IgA (8) and IgM (6). The species and stage specificity of 15 of these monoclonal antibodies were determined by ELISA. These results are summarized in Table 1. Thirteen of the 15 monoclonals reacted with both the crude extract of $L_1$ (CWE) and with the adult extract of *T. spiralis* but not with ES products of the $L_1$ stage. Eleven of the 13 monoclonals which reacted with the *T. spiralis* adult extract also reacted with antigens of two or more other parasite species. Those clones reacting with the *A. suum* larval antigen also reacted with the *S. ransomi* larval extract, as well as other life cycle states of *A. suum*. Those clones reacting with the *A. suum* egg antigen also reacted in all cases with the *S. dentatus* adult extract, and usually with the *A. suum* adult extract. All clones reacting with the *T. spiralis* adult extract also reacted with the extract of *T. suis*, including two clones which did not react with any of the other parasites tested ($1A_5C_3$ and $7B_4C_5$). One clone ($1C_2C_1$) reacted with the *T. spiralis* $L_1$ extract and ES products of the larvae, but not with any of the other parasite extracts; this clone also reacted weakly with the *T. spiralis* adult extract. One other clone ($7C_2C_5$) reacted exclusively with the *T. spiralis* $L_1$ extract and ES products. Because of the lack of reactivity with other parasite antigens, specificity for ES products, and superior growth characteristics, $7C_2C_5$ was selected as the clone to provide a diagnostic reagent for swine trichinosis.

Immunochemical characterization of monoclonals—Hybrid line 7C₂C₅ secreted a *T. spiralis*-specific IgM antibody molecule as determined by gel diffusion and autoradiography of SDS-gels of reduced $S^{35}$ labelled antibody. When used in an agglutination assay with ES coated SRBC's, 7C₂C₅ ascites fluid agglutinated cells with an end-point titer of 1:10,000. Following mild reduction with cysteine this titer was reduced to 1:100, indicating that a multimeric form of the IgM molecule had been reduced. When passed through a gel filtration column, antibody activity as determined by ELISA appeared in fractions corresponding to both pentameric and monomeric IgM as determined by reference standards.

The protein molecular weight specificity of hybridoma 7C₂C₅ was determined by immunoreplicate electrophoresis and western blot immunoenzyme techniques. *T. spiralis* ES products separated in SDS-polyacrylamide gels were analyzed with ascites fluid from monoclonal 7C₂C₅ or P3X. Using immunoreplicate electrophoresis three protein bands were visible in reduced gels overlaid with 7C₂C₅ both before and after staining, with approximate apparent molecular weights of 53,000, 49,000 and 45,000. No bands appeared in the P3X controls. These same three bands were seen in nitrocellulose strips reacted with ascites fluid from hybridoma 7C₂C₅. An additional non-specific band was on present 7C₂C₅ and P3X reacted strips.

In vitro effect of monoclonal antibody on live *T. sprialis* larvae- Freshly isolated *T. spiralis* $L_1$ were incubated with normal and immune pig sera, P3X ascites fluid, and ascites fluid from hybrid 7C₂C₅. In normal pig sera and P3X ascites fluid after 12-hour incubation at 37° C. worms appeared normal and active with no visible precipitation reactions. In immune pig sera and 7C₂C₅ ascites fluid large precipitates accumulated and adhered to the oral end of the worms.

Reactivity of monoclonal antibody with worm sections—Hybridoma 7C₂C₅ bound specifically to a component present in the *T. spiralis* stichcyte gland as determined by immunoperoxidase staining procedures. No non-specific reactions were seen with control P3X ascites fluid.

Affinity purification of antigen—Antibody from clone 7C₂C₅ ascites, partially purified by precipitation in 50% ammonium sulfate, was coupled to Sepharose 4B and used as an affinity-ligand to isolate antigen. From 4 mg of ES products, 312 µg were specifically bound and recovered from the column. Specifically bound protein was analyzed on SDS-polyacrylamide gels under reducing conditions. Two doublet protein bands of approximate apparent MW of 53,000 and 49,000 appeared. In addition, a protein band of approximate molecular weight of 67,000 was also present, and presumably represented minor amounts of eluted monoclonal antibody (µ chain).

ELISA with affinity purified antigen—Crude worm extract or antigen isolated by affinity chromatography using monoclonal 7C₂C₅was diluted in ELISA coating buffer and bound to microtiter plates for use in the ELISA test. Sera tested included a normal pool, sera from *T. spiralis*-negative pigs known to yield false-positive reactions in the ELISA using crude worm extract as antigen, and sera from pigs experimentally-infected with *T. spiralis*. When the crude extract was used as antigen, 11 of 35 sera (31%) gave positive values. When the ES antigen purified with monoclonal antibody 7C₂C₅ was used as antigen all of the false-positive reactions were eliminated. In addition, the monoclonal-affinity antigen reliably detected all infected animals and provided a good separation of the two groups (negative mean O.D.=0.050; positive mean O.D.=0.461).

As noted above, an alternative to the indirect test is a competitive ELISA in which serum antibodies compete with monoclonal antibodies for antigen bound to microtiter plates. We developed an assay for serum antibodies directed against *T. spiralis* using a biotinylated monoclonal antibody and an avidin-enzyme conjugate.

For use in the competitive ELISA, monoclonal antibody from hybridoma 7C₂C₅ was produced in murine ascites fluid, partially purified by precipitation in 50% ammonium sulfate, and biotinylated according to methods described in J. Histochem. Cytochem. 28, 771–776, 1980. An ES preparation in saline was prepared from *T. spiralis* muscle larvae as in Vet. Parasitol. 13, 349–361, 1983.

*T. spiralis* ES proteins Ts.49 and Ts.53 were obtained from crude ES by affinity chromatography on a 7C₂C₅ monoclonal antibody-Sepharose 4B affinity column as described above. Rabbit anti-swine IgG (γ-chain specific) was prepared as described in Vet. Parasitol. 13, 349–361, 1983. Goat anti-rabbit IgG conjugated to horseradish peroxidase was obtained from a commercial source.

Polystyrene microtiter plates were coated overnight at 4° C. with 100 µl well of ES products diluted to 2 µg/ml in 0.1M carbonate buffer (pH 9.6). Following coating, and between all subsequent steps, wells were washed three times (five minutes each) with 0.05M phosphate buffer (pH 8.0) containing 0.5M NaCl and 0.1% Tween 20 (wash buffer). The high pH and salt content of the buffer reduces non-specific binding. Under these conditions, post-coating was unnecessary.

To optimize reagent concentrations, titration experiments were performed. Biotin-labelled antibody, 100 µl of various concentrations diluted in wash buffer, was added to coated wells, and the plates were incubated at room temperature (RT) for one hour. Following washing, 100 µl of an avidin-peroxidase conjugate diluted to various concentrations in wash buffer was added and incubation repeated. Finally, the plates were washed, and 100 µl of substrate-indicator solution, 5'-aminosalycylic acid (pH 5.6)+0.005% $H_2O_2$, was added. Plates were read at 15 minutes in a Titertek Multiscan.

Titrations were performed initially on the biotin-antibody conjugate with excess avidin-enzyme, and subsequently on the avidin-enzyme in the presence of optimal dilutions of biotin-antibody conjugate. Biotin-antibody dilutions were used such that 80–100% of maximum binding to antigen was achieved. Avidin-peroxidase was used at a concentration that allowed 100% of bound biotin to be detected.

For the competitive assay, 50 µl of the biotin-antibody conjugate at 2×the optimal dilution and 50 µl of pig serum, undiluted or diluted 1:5 in wash buffer, were added to antigen coated wells. Final serum dilution was 1:2 or 1:10. In some experiments, the serum and biotin-antibody conjugate were incubated together for one hour at RT prior to addition to wells and in other experiments these reagents were added sequentially. The assay was completed as described above, and the percent inhibition was calculated based on control values (optical density, O.D.) of the normal serum pool (NSP) for each experiment as follows:

$$\% I = 100 - \frac{O.D. \text{ of sample}}{O.D. \text{ of NSP}}$$

Additional controls for each assay included biotin-antibody conjugate and avidin-enzyme without serum, and avidin-enzyme only.

A triple-antibody indirect ELISA was performed using monoclonal antibody affinity-isolated antigen as described in Vet. Parasitol. 13, 349-361, 1983.

A normal serum pool was collected from eight pigs, two-months-old, from the SPF herd at API, Beltsville, Md, with no prior exposure to helminth infection. Serum was collected from 30 six-month-old pigs inoculated with 10,000 infective T. spiralis muscle larvae at two months of age. Serum was collected from 35 six-month-old, farm-raised slaughter pigs that were found to be negative for T. spiralis by the digestion technique. These same 35 sera had previously been shown to give false-positive reactions in an ELISA when a crude T. spiralis extract was used as antigen. Thirteen sera were collected from pigs with natural infections of Trichurus suis; worm burdens in these pigs were variable, however, all 13 sera gave strongly positive results for anti-T. suis antibody in an indirect ELISA. A pool of serum was collected from pigs with naturally-acquired infections of Ascaris suum as determined by fecal and post mortem examination. Serum pools were also collected from pigs experimentally infected with Strongyloides ransomi (inoculated with 25,000 to 50,000 $L_3$ larvae three months prior to blood collection) and Stephanurus dentatus (inoculated with 14,000 $L_3$ larvae four months prior to blood collection).

Two other groups of experimentally-infected pigs were used to determine the temporal appearance of T. spiralis-specific antibody. One group of two-month-old pigs (n=8) each received 10,000 T. spiralis muscle larvae and were serially bled on days 10, 15, 20, 25 and 30 postinoculation; worm burdens were determined by the digestion technique at the end of the experiment. A second group of two-month-old pigs (n=24) each received 500 T. spiralis muscle larvae, and groups of four pigs were killed, serum collected and worm burdens determined on days 10, 18, 25, 36, 50 and 80 postinoculation.

A group of sera were obtained from farm-raised pigs with naturally-acquired infections of T. spiralis. Larval densities as determined by digestion of tongue and diaphragm tissue varied from 0.1-660 larvae per gram (LPG).

Optimal reagent concentrations for the competitive ELISA were determined to be 3.6 μg/ml of the biotin-antibody conjugate and 2.9 μg/ml of the avidin-peroxidase conjugate. Values obtained for NSP or for biotin-antibody and avidin-enzyme without serum were not significantly different. Values for avid-enzyme only did not differ significantly from zero, indicating a lack of non-specific binding to the plate.

The influence of preincubation of serum samples with biotin-antibody conjugate prior to addition to antigen-coated wells or sequential addition of serum and biotin-antibody conjugate was examined Table 2 ). Similar inhibition values were obtained with these methods as compared to simultaneous addition of serum and antibody conjugate with no preincubation (P>0.005).

As a direct test for the presence of parasite antigen or immune-complexes in serum samples, an ELISA was performed in wells coated with normal or T. spiralis-infected pig serum, and then reacted with biotinylated monoclonal antibody and avidin-enzyme conjugate (Table 3). No positive reactions were obtained with sera from pigs experimentally infected with T. spiralis.

Data were obtained with sera from 35 farm-raised, T. spiralis digestion-negative pigs, 30 T. spiralis-positive (experimentally-infected) pigs and pigs with experimental or naturally-acquired infections of T. suis, A. suum, S. ransomi and S. dentatus in the competitive ELISA. The mean of inhibitory values for positive pigs was 82%±1.7% (x+/−S.E.) with a range of 58-98%. The mean of inhibitory values for T. spiralis-negative pigs was 2.3%+/−0.7% with a range of 0-16%. No inhibition was found with sera from pigs infected with T. suis (1.4%+/−0.9%), A. suum (0%), S. ransomi (0.2%) or S. dentatus (0%).

Sera were collected from two groups of pigs experimentally infected with a high (10,000 $L_1$) or low dose (500 $L_1$) of T. spiralis, and the temporal appearance of antiparasite host antibodies was determined using the competitive ELISA at serum dilutions of 1:10 and 1:2, Table 4. A positive cut-off was established at 2×the mean of a random group of ten serum samples from T. spiralis-negative farm-raised pigs. A serum dilution of 1:2 was more effective in detecting early seroconversions (day ten for high dose); all infected animals were detected by 25 and 36 days post-infection in the high and low dose groups, respectively.

A comparison of the competitive and indirect ELISA using sera from naturally-infected pigs was made. A group of 30 pigs with naturally-acquired infections of T spiralis was tested in both the competitive ELISA and the indirect ELISA. A group of ten randomly selected sera from farm-raised T. spiralis-negative pigs was included as a control. Serum samples for the indirect ELISA were tested at dilutions of 1:10 and 1:100. Serum samples for the competitive ELISA were tested at 1:2 and 1:10 (final dilution). In the competitive ELISA a dilution of 1:10 was ineffective in detection of positive serum samples. At a 1:2 dilution in the competitive ELISA, all serum samples from infected pigs gave inhibitory values which exceeded 2×the mean and the range of ten serum samples from T. spiralis-negative farm-raised pigs. Identical results were obtained using the indirect ELISA at both 1:10 and 1:100 serum dilutions.

As demonstrated above, the competitive ELISA offers several advantages over incirect ELISA procedures. First, it eliminates the need to prepare affinity-isolated antigen. Second, the assay maintains strict specificity, limited to serum antibodies reacting with the antigen epitope recognized by the monoclonal antibody. The interactions of other serum antibodies with other antigen epitopes in the ES preparation are not involved in the assay. Finally, variation may be reduced since all antigen-antibody interactions occur in one step; subsequent amplification occurs by the binding of the avidin-enzyme conjugate to biotinylated antibody.

The competitive assay, using biotinylated monoclonal antibody $7C_2C_5$, performed as well as an indirect ELISA using monoclonal antibody affinity-isolated antigen. High background values and false-positive reactions were eliminated in sera from T. spiralis-negative farm-raised slaughter pigs. Additionally, no false-positive reactions were obtained with sera from pigs with naturally-acquired infections of T. suis or A. suum or experimentally infected with S. ransomi or S. dentatus. Infections of these swine nematodes, particularly the closely related *T. suis*, would be the most likely cause of cross-reactions in diagnostic tests for *T. spiralis*. The competitive ELISA reliably detected all pigs experimentally infected with *T. spiralis.*

The competitive ELISA detected seroconversions in experimentally-infected animals in a manner comparable to results obtained using amplified indirect assays, Vet. Parasitol. 13, 349-361, 1983. Pigs receiving relatively high doses of *T. spiralis* muscle larvae (10,000) were identified as positive as early as day 10 postinfection, while all pigs receiving this dose were positive by day 25 postinfection. At a lower dose (500 $L_1$) all infected pigs were detected by day 36 postinfection.

The inhibitory effect of serum from *T. spiralis*-infected pigs on the binding of monoclonal antibody in the competitive ELISA was shown to be due exclusively to the presense of host serum antibodies, rather than circulating parasite antigens or immune complexes. Inhibition of the binding of biotinylated monoclonal antibody $7C_2C_5$ occurred whether serum was added simultaneously or in a prior step. Blocking of binding due to interactions of the monoclonal antibody with serum antigen would require that the monoclonal and the serum be combined. In addition, no parasite antigen was detected in a direct ELISA for antigen in serum samples from *T spiralis*-infected pigs.

TABLE 1

| | *T. spiralis* | | | *A. suum* | | | *S. ransomi* | *S. dentatus* | *T. suis* |
|---|---|---|---|---|---|---|---|---|---|
| Clone | larvae | adult | ES* | larvae | adult | egg | larvae | adult | adult |
| $1A_5C_3$ | + | + | − | − | − | − | − | − | + |
| $1B_2C_1$ | + | + | − | − | − | + | − | + | + |
| $1C_2C_1$ | + | + | + | − | − | − | − | − | − |
| $1D_3C_3$ | + | + | − | + | + | + | − | + | + |
| $7A_4C_2$ | + | + | − | + | + | + | − | + | − |
| $7A_5C_1$ | + | + | − | − | − | + | − | + | + |
| $7A_6C_1$ | + | + | − | + | + | + | + | + | + |
| $7B_1C_3$ | + | + | − | + | − | + | + | + | + |
| $7B_3C_2$ | + | + | − | − | + | + | − | + | + |
| $7B_4C_5$ | + | + | − | − | − | − | − | − | + |
| $7C_2C_5$ | + | − | + | − | − | − | − | − | − |
| $7C_5C_2$ | + | + | − | + | + | + | + | + | + |
| $7D_1C_2$ | + | + | − | − | + | + | − | + | + |
| $7D_4C_1$ | + | + | − | − | + | + | − | + | + |
| $7D_5C_2$ | + | + | − | − | + | + | − | + | + |

*ES — excretory secretory products
ELISA O.D. values greater than 5 times the P3X control were considered positive.

TABLE 2

| Treatment | % Inhibition (+/− S.E) |
|---|---|
| No preincubation, reagents added simultaneously | 75.0[a] +/− 3.2 |
| Sera and biotinylated monoclonal antibody preincubated for 60 min. (37° C.) | 76.5[a] +/− 5.1 |
| Serum sample added to well, incubated 60 min., wells washed and biotinylated monoclonal antibody added | 68.8[a] +/− 3.5 |

[a]Mean of sera from 6 pigs experimentally infected with 10,000 *T. spiralis* muscle larvae and bled 6 months later TABLE 3[a]

| Antigen bound to plate | ELISA O.D. Values |
|---|---|
| Normal swine serum | 0.016 |
| ES antigen (0.5 μg/well) | 0.225 |
| Serum from pigs experimentally infected with *T. spiralis* | 0.023[b] +/− 0.002 (S.E.) |

[a]Serum from pigs experimentally infected with *T. spiralis* was diluted 1:1 in ELISA coating buffer and incubated overnight in microtiter wells at 4° C. Wells were washed and reacted with biotinylated monoclonal antibody $7C_2C_5$ for one hour, and the assay was completed as described in the text.
[b]Mean of sera from ten pigs experimentally infected with 10,000 *T. spiralis* muscle larvae and bled six months later.

TABLE 4

| | Serum dilution | | |
|---|---|---|---|
| Day post-infection | 1:10 | 1:2 | LPG[a] |
| High dose (10,000 muscle larvae) | | | |
| 10 | 0/8[b] | 4/8 | N.D.[c] |
| 15 | 1/8 | 5/8 | N.D. |
| 20 | 2/8 | 6/8 | N.D. |
| 25 | 7/8 | 8/8 | N.D. |
| 30 | 8/8 | 8/8 | 418 |
| Low dose (500 muscle larvae) | | | |
| 10 | 0/4[b] | 0/4 | 0 |
| 18 | 0/4 | 0/4 | 0 |
| 25 | 0/4 | 1/4 | 55 |
| 36 | 3/4 | 4/4 | 101 |
| 50 | 3/4 | 4/4 | 73 |
| 80 | 4/4 | 4/4 | 35 |

[a]Larvae per gram of diaphragm tissue at necropsy.
[b]Number of pigs positive/number of pigs tested.
[c]Not done.

We claim:

1. A hybridoma formed by the fusion of a mouse spleen cell with a mouse myeloma cell, said hybridoma being designated as ATCCHB8678.

2. A monoclonal antibody secreted by hybridoma ATCCH38678 said antibody being characterized by its ability to recognize an antigen epitope present on proteins of molecular weights 53,000 49,000 and 45,000 from *Trichinella spiralis,* said antigen being unique to *Trichinella spiralis.*

3. A method for isolating three specific proteins from a crude extract of homogenized *Trichinella spiralis* muscle larvae ($L_1$) or from excretory-secretory products of the muscle larvae obtained by culturing *T. sprialis* in tissue culture media, comprising:

(a) covalently linking hybridoma ATCCHB8678 produced antibodies to a cross-linked dextran gel;

(b) passing said crude *T. spiralis* extract or secretary products over said covalently linked antibodies and allowing proteins specific to *T. spiralis* to bind to said antibodies, said proteins having molecular weights of 53,000 49,000 and 45,000, and being designated Ts.53, Ts.49, and Ts.45; and (c) eluting and collecting said specifically bound proteins.

4. A method for detecting *Trichinella spiralis* infection in swine, comprising:
   (a) coating a plastic surface of a well of a plate or a tube with an excretory-secretory preparation derived from in vitro cultivation of *T. spiralis* muscle larvae ($L_1$);
   (b) mixing biotin-labeled monoclonal antibody produced by hybridoma ATCCHB8678 with a swine serum sample and applying it to said antigen coated plastic surface of step (a);
   (c) incubating said applied mixture of step (b), allowing swine antibodies specific for *T. spiralis* to bind with said antigen coated plastic surface, and washing away material which does not bind;
   (d) adding an avidin-enzyme conjugate to the well or tube, incubating, and allowing said avidin-enzyme conjugate to bind with said biotin-labeled monoclonal antibody produced by hybridoma ATCCHB8678, washing away unbound avidin-enzyme conjugate, and adding an enzyme indicator substrate; and
   (e) determining infection by recording a reduction in color change by said enzyme substrate, that reduction in color change indicating the presence of *T. spiralis* specific swine serum antibodies which have competed for antigenic binding sites with the monoclonal antibody.

* * * * *